United States Patent [19]

Bumpus et al.

[11] 3,976,770

[45] Aug. 24, 1976

[54] SAR'-(OME)THR[8] ANGIOTENSIN II AS AN ANGIOTENSIN II ANTAGONIST

[76] Inventors: Francis Merlin Bumpus, 75 Winterberry Lane, Chagrin Falls, Ohio 44022; Mahesh Chandra Khosla, 7415 Warwick Lane, Chesterland, Ohio 44026; Robert Rudolph Smeby, 36801 Riviera Road, Willoughby, Ohio 44094

[22] Filed: Feb. 10, 1975

[21] Appl. No.: 548,328

[52] U.S. Cl. .......................... 424/177; 260/112.5 R
[51] Int. Cl.[2] ................. A61K 37/00; C07C 103/52
[58] Field of Search .............................. 260/112.5 R

[56] References Cited

UNITED STATES PATENTS 3,886,134  5/1975  Sipos et al..................... 260/112.5 R

*Primary Examiner*—Lewis Gotts
*Assistant Examiner*—Reginald J. Suyat
*Attorney, Agent, or Firm*—Paul D. Burgauer; Robert L. Niblack

[57] ABSTRACT

A new octapeptide having profound angiotensin antagonist properties has been found. The new compound resembles angiotensin II except for the two terminal amino acids, carrying unnatural amino acids at the N-terminus, and at the C-terminus.

4 Claims, No Drawings

SAR'-(OME)THR⁸ ANGIOTENSIN II AS AN ANGIOTENSIN II ANTAGONIST

DETAILED DESCRIPTION OF THE INVENTION

This invention relates to polypeptides. More particularly, it is concerned with the octapeptide of the formula:

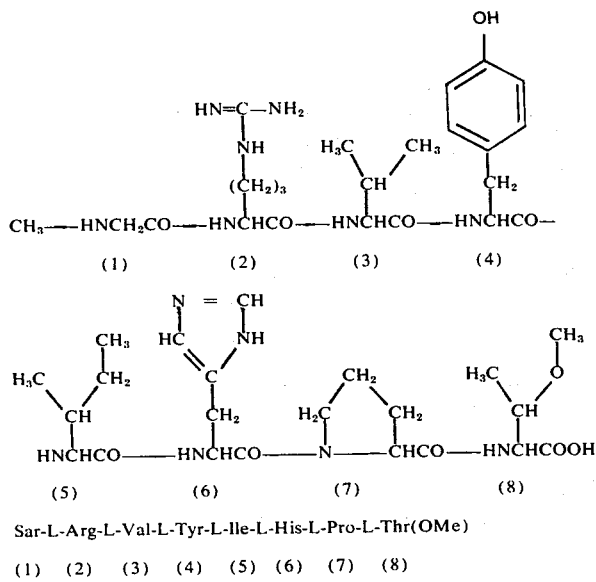

Sar-L-Arg-L-Val-L-Tyr-L-Ile-L-His-L-Pro-L-Thr(OMe)
(1)  (2)   (3)  (4)  (5)  (6)  (7)   (8)

The peptide of this invention possesses valuable pharmacological activity. It is capable of inhibiting the pressor effect of angiotensin II. Thus, when administered by intravenous infusion into rats in a very small amount, the pressor effect of angiotensin II is inhibited. By virtue of this inhibitory property upon angiotensin II induced blood pressure elevation, the peptide of this invention is a valuable agent for counteracting hypertension due to angiotensin II. It is also capable of reducing blood pressure in acute unilateral renal hypertensive rats upon intravenous infusion.

The octapeptide of this invention is readily prepared in accordance with known methods for preparing peptides. Such methods involve the building of a linear chain of amino acids through repetitive amide linkages employing in such sequential alignment the necessary protective groups susceptible to ready removal by conventional cleavage methods which do not affect the peptide bonds. The adaptation of such methods to the peptide of this invention is described in the example below. All the amino acids used in the above structure of Formula I are in the L-configuration. The corresponding chain with D-amino acids does not show the pharmacological effect described below.

In order to illustrate the method for making the compound of structure I, reference is made to the following example, which however, is not intended to limit the invention in any respect. In this example, the abbreviation BOC— is used in its accepted meaning, referring to tertiary butyloxycarbonyl. It also should be understood that all amino acids used in this example are in their L-configuration. The BOC- amino acids used below are either commercially available or were prepared according to the method of Schwyzer et al., Helv. Chim. Acta 42, 2622 (1959).

EXAMPLE

A solution of 1.97 g of BOC-(0-methylthreonine) and 1.3 ml of triethylamine in 50 ml of ethanol was added to 9 g of chloromethylpolystyrene/divinylbenzene (98:2) copolymer of a mesh size between 200 and 400, containing 5.02% chlorine. The mixture was stirred at 80°C for 36 hours. The esterified polymer was filtered, washed several times in sequence with ethanol, dilute acetic acid, water, ethanol and methanol. The polymer was dried in vacuo over phosphorous pentoxide. Hydrolysis of an aliquot of the polymer and subsequent amino acid analysis indicated that 0.56 millimoles of BOC-(0-methyl)-threonine were esterified per gram of the polymer. Further coupling of the BOC-proline, BOC-N-imidazolebenzyl-histidine, BOC-isoleucine, BOC-(0-benzyl)-tryosine, BOC-valine, BOC-nitroarginine and BOC-sarcosine in the respective order was carried out by utilizing the action given below for each amino acid residue. Unless specified, all washings were carried out three times for three minutes each, first with glacial acetic acid and second with methylene chloride. The BOC group was removed by treatment with 40% (volume/volume) of trifluoroacetic acid in methylene chloride for 30 minutes, preceded by a prewash with this reagent for 3 minutes to avoid dilution of the trifluoroacetic acid by the previous methylene chloride wash. The deprotected amino acid polymer ester was washed five times for 3 minutes each with chloroform and the trifluoroacetate salt neutralized by treating the residue for 7 minutes with 10% triethylamine in chloroform, followed by three 3 minute washings with chloroform and methylene chloride in sequence. The subsequent incoming BOC-amino acid was added in a 2-fold excess in methylene chloride and the mixture was stirred for 10 minutes. In the case of BOC-nitroarginine and BOC-benzyl histidine, these materials were first dissolved in dimethylformamide, followed by filtration and mixing the filtrate with onethird volume of methylene chloride. Both of these derivatives were used in 3-fold excesses. Coupling was aided in each instance by the addition of a 2-fold excess of dicyclohexylcarbodiimide in methylene chloride and mixing was carried out for 2.5 hours except in the coupling steps involving Arg or His where DCI was used in a 3-fold excess and mixing allowed for eight hours. The polymer-peptide chain was then washed with DMF followed by a washing with DMF/methylene chloride (1:1) and the coupling step with the BOC-amino acid and DCI was repeated using a mixture of 1:1 DMF/methylene chloride as the solvent. The polymer chain was then washed with methanol to remove dicyclohexylurea and finally washed with DMF. Completeness of each coupling at intermediate stages was checked by known color reaction tests. The apparatus used for the above synthesis was of the manual type described by Khosla, Smeby and Bumpus, Science 156, 253 (1967). All couplings were carried out at 0° – 5°C to avoid racemization; 1 hydroxybenzotriazole was used as an additive to minimize racemization of histidine during the coupling of BOC-imidazolebenzyl histidine [see G. C. Windridge and E. C. Jorgensen, J.A.C.S., 93, 6318 (1971)].

In the above sequence, the blocked (protected) amino acids were coupled in sequence to the 0-methyl threonine-polymer, using BOC-proline, BOC-N-imidazole-benzyl-histidine, BOC-isoleucine, BOC-(0-benzyl)-tyrosine, BOC-valine and BOC nitroarginine and BOC-sarcosine to produce a peptide of the structure of Formula I with amino acids 1 – 8 bound to the polymer substrate.

The protected peptide polymer was suspended in approximately 100 ml of freshly distilled trifluoroacetic acid and a slow stream of hydrogen bromide, prewashed with 10% resorcinol in acetic acid, was passed through the suspension under anhydrous conditions for about 30 minutes with occasional shaking. The suspension was filtered and the polymer was washed with trifluoroacetic acid. The combined filtrates were evaporated at room temperature in vacuo. The amorphous powder was washed with ether, dissolved in a mixture of methanol/acetic acid/water 5:1:1 and the solution hydrogenated at 3.5 kg/cm$^2$ over 0.5 parts of palladium black per part of peptide weight for 48 hours with shaking. The product was purified on a 2.5 × 100 cm column of Sephadex G 25 (a partially cross-linked dextran gel having an exclusion of molecular weight sizes of >5000, marketed by Pharmacia of Uppsala, Sweden) using n-butanol/water/pyridine (10:5:2) as the developing solvent. Fractions in column chromatography were cut without regard for yield to obtain the desired compound in the pure form and no attempt was made to rechromatograph the minor fractions for identification purposes. The average yield of the product obtained in this manner varied between 40 and 60% based on the millimoles of C-terminal amino acid esterified onto the polymer. The homogeneity of the compound was determined by the thin-layer chromatography in various solvent systems of different pH, electrophoresis at pH 1.95 and 8.6 and amino acid analysis, proving that the compound is homogeneous with $R_f$ 0.33 (n-butanol/acetic acid/water 4:1:5 upperphase) and $R_f$ 0.67 (n-butanol/ethylacetate/acetic acid/water 1:1:1:1), $R_f$ 0.13 (n-butanol/pyridine/water 10:2:5), $R_f$ 0.58 (n-butanol/acetic acid/water/pyridine 15:3:12:10) on cellulose thin-layer plates. The chemical analysis showed that the required amino acids were present in the expected ratio.

The above antagonist was studied both in vitro and in vivo. The in vitro assay mainly evolves around an assay of isolated rabbit aortic strips mounted in a muscle bath in 5 ml of Krebs' solution.

The strips were placed under 2 grams of passive tension and allowed to equilibrate for 1.5 – 2 hours. Cumulative dose-response curves were obtained for angiotensin II at concentrations of 1 to 64 ng/ml. The antagonist was added to the bath at a certain concentration, allowed to equilibrate for 5 minutes and the response to angiotensin II again tested. The various doses of the antagonist thus tested were 1, 10, 100 and 1000 ng/ml. Changes in these curves were plotted and measurement of shift to the right of the dose-response curve were measured. At the same time, it was assured that the maximal response of the tissue remained unchanged. At the end of the experimental period the antagonist was washed out and cumulative dose-response curves were repeated again. Results of these studies are expressed in the form of $pA_2$ values as defined by O. Arunlakshna and H. O. Schild, Brit. J. Pharmacol. 14, 48 (1959). The compound for Formula I showed a $pA_2$ value of 8.76 ± 0.08.

In the in vivo assays, rats were anesthetized with sodium amytal and further treated with 0.6 mg atropine and pentolinium tartrate. They were vagotomized and direct recording of the blood pressure was measured through the carotid artery, while the femoral artery was used for infusing the desired dose over a period of 30 minutes in a physiological saline solution.

The dose-response curves of angiotensin II at 0.9 to 54 ng/kg/min. were compared by linear regression analysis with those of the antagonist at doses of 1, 10, 100 and 1000 ng/kg/min. Infusion of the above antagonist into rats thus prepared led to the initial transient pressor response of 0.48 on a scale set artificially at 100 for angiotensin II using the same system.

For determining its antagonistic properties the compound was infused intravenously in ganglion blocked rats at a dose level of 125, 250, 500, 1250 ng/kg/min. The blocking effect of the compound was calculated from the dose-response curve of angiotensin II before and during the infusion of the analog. General procedure adopted for this assay has been described by Bumpus et al., Circ. Res. 32–33 (Supplement I), I–150 (1973). The compound blocked the pressor response of angiotensin II at a dose level of 125 ng/kg/min or greater. The dose-ratio obtained was 62.50 ± 14.93 at a dose-level of 250 ng/kg/min.

Since the above compound is particularly suitable for injection or infusion, it is particularly valuable that the compound is watersoluble. A suitable dosage unit can be prepared by simply dissolving the above compound in water or physiological saline at a concentration of between 50 and 6000 ng/ml. Such a solution can be administered directly or it can be stored under proper conditions for periods of several weeks without deterioration, particularly when combined with 1 - 5% of a preservative such as benzyl alcohol and/or is buffered to a suitable pH with a nontoxic, pharmaceutically acceptable buffer. A commonly employed buffer for an injectable solution is Tris(hydroxymethyl) aminomethane but simple salts such as sodium phosphate or acetate can be used. Preferably, the vehicle or medium in which the compound of Formula I is dissolved for an injectable or infusable solution is buffered to a pH of 7 to 7.5.

The duration of action of the compound can be prolonged by injecting an oil solution intramuscularly. Oils suitable for this purpose are cod liver oil, sesame oil, refined coconut oil, etc. Antagonistic effects are thus observed for 24 hours or longer after a single i.m. injection of the drug dissolved in such an oil.

What is claimed is:

1. The octapeptide Sar-L-Arg-L-Val-L-Tyr-L-Ile-L-His-L-Pro- -(OMe)Thr.

2. A composition suitable for parenteral administration to a warm-blooded animal consisting essentially of the octapeptide of claim 1 dissolved in a liquid, pharmaceutically acceptable vehicle suitable for injection into warm-blooded animals, said octapeptide being present at a concentration of between 50 and 6000 ng/ml of said vehicle.

3. The composition of of claim 2 wherein said vehicle is water buffered to a pH of 7 to 7.5.

4. The composition of claim 2 wherein said vehicle is an oil solution.

* * * * *